(12) United States Patent
Green et al.

(10) Patent No.: US 6,846,283 B2
(45) Date of Patent: Jan. 25, 2005

(54) METHODS AND APPARATUS FOR LOADING RADIOACTIVE SEEDS INTO BRACHYTHERAPY NEEDLES

(75) Inventors: Thomas C. Green, Seattle, WA (US); Ryan P. Boucher, San Francisco, CA (US); Yuri Belman, Sunnyvale, CA (US)

(73) Assignee: Neoseed Technology LLC, San Francisco, CA (US)

( * ) Notice: Subject to any disclaimer, the term of this patent is extended or adjusted under 35 U.S.C. 154(b) by 0 days.

(21) Appl. No.: 10/134,098

(22) Filed: Apr. 25, 2002

(65) Prior Publication Data

US 2004/0162458 A1 Aug. 19, 2004

Related U.S. Application Data

(63) Continuation of application No. 09/998,610, filed on Nov. 29, 2001, now Pat. No. 6,638,206, which is a continuation of application No. 09/522,248, filed on Mar. 9, 2000, now Pat. No. 6,358,195.

(51) Int. Cl.[7] .............................................. A61N 5/00
(52) U.S. Cl. .......................................................... 600/7
(58) Field of Search ......................................... 600/1–8

(56) References Cited

U.S. PATENT DOCUMENTS

| 4,086,914 A | 5/1978 | Moore |
| 4,167,179 A | 9/1979 | Kirsch |
| 4,700,692 A | 10/1987 | Baumgartner |
| 4,815,449 A | 3/1989 | Horowitz |
| 5,460,592 A | 10/1995 | Langton et al. |
| 5,928,130 A | 7/1999 | Schmidt |
| 6,036,631 A | 3/2000 | McGrath et al. |
| 6,083,166 A | 7/2000 | Holdaway et al. |
| 6,213,932 B1 | 4/2001 | Schmidt |

FOREIGN PATENT DOCUMENTS

| SU | 279-814 | * 11/1975 | .................. 600/7 |
| WO | WO 99/20337 | 4/1999 | |

OTHER PUBLICATIONS

Peter Grimm, "Ultrasound Guided Implantation of the Prostate: A Practical Review Course", 5/99.

* cited by examiner

Primary Examiner—John P. Lacyk
(74) Attorney, Agent, or Firm—Fish & Neave; Douglas A. Oguss

(57) ABSTRACT

Methods and apparatus are provided for loading therapeutic materials into brachytherapy needles. The apparatus comprises an apparatus with chambers, and radioactive seed and spacer cartridges received therein. The apparatus may be used in conjunction with a standard brachytherapy needle coupled to the distal end of the apparatus. The plunger dislodges seeds and spacers from the cartridge chambers to load the needle with a predetermined packing arrangement.

34 Claims, 13 Drawing Sheets

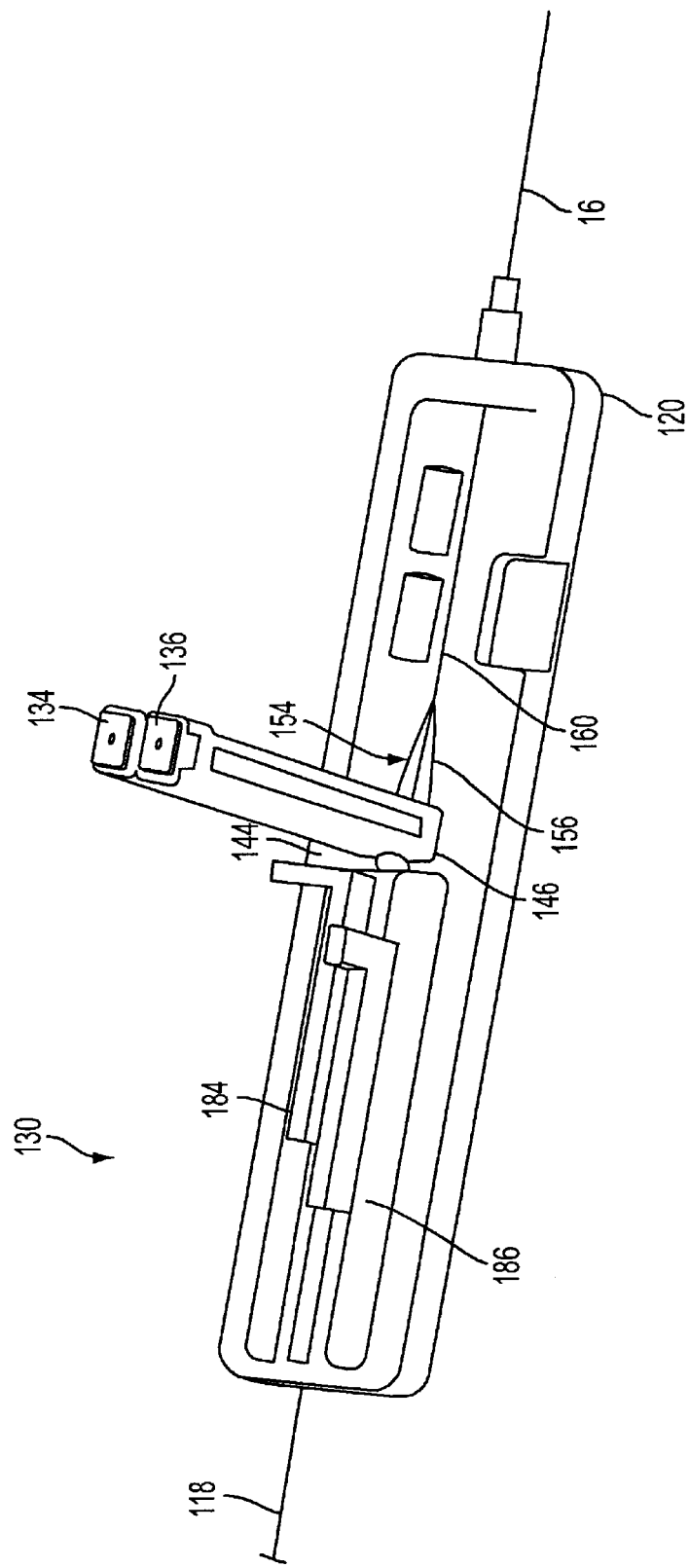

METHODS AND APPARATUS FOR LOADING RADIOACTIVE SEEDS INTO BRACHYTHERAPY NEEDLES

REFERENCE TO RELATED APPLICATIONS

The present application is a continuation-in-part of U.S. patent application Ser. No. 09/998,610, filed Nov. 29, 2001, now U.S. Pat. No. 6,638,206 which is a continuation of U.S. patent application Ser. No. 09/522,248, filed Mar. 9, 2000, now U.S. Pat. No. 6,358,195 both of which are hereby incorporated herein by reference.

FIELD OF THE INVENTION

This invention relates to improved apparatus and methods for the treatment of prostate cancer. More particularly, the present invention provides improved methods and apparatus for loading radioactive seeds into brachytherapy needles.

BACKGROUND OF THE INVENTION

Excluding non-melanoma skin cancers, prostate cancer is the most common cancer afflicting American men. The American Cancer Society estimates that over 198,100 new cases will be diagnosed in the U.S. in the year 2001 alone, and that nearly 31,500 people will die from the disease. Prostate cancer is second only to lung cancer as the leading cause of cancer death in men, accounting for roughly 12%.

Prostate cancer is defined as malignant tumor growth within the prostate gland. Its cause is unknown, although high dietary fat intake and increased testosterone levels are believed to be contributory factors. A letter scale ("A" through "D"), which accounts for the location of the cancer, is commonly used to classify the stage of disease. In Stage A, the tumor is not palpable but is detectable in microscopic biopsy. Stage B is characterized by a palpable tumor confined to the prostate. By Stage C, the tumor extends locally beyond the prostate with no distant metastasis. By Stage D, cancer has spread to the regional lymph nodes or has produced distant metastasis.

In the early stages, prostate cancer is most commonly treated by prostate removal or by brachytherapy. More advanced cases are treated by medical hormonal manipulation or orchiectomy to reduce testosterone levels and curb spreading of the disease, by chemotherapy, or by external beam radiation therapy.

With regard to treatment of early stage prostate cancer, the state of the art has several drawbacks. Radical prostatectomy is often recommended for treatment of localized stage A and B prostate cancers. Under general or spinal anesthesia, an incision is made through a patient's abdomen or perineal area, and the diseased prostate is removed. The procedure is lengthy, especially if a lymph node dissection is simultaneously performed, and requires a hospital stay of 2–5 days. Possible complications include impotence and urinary incontinence.

Internal radiation therapy or brachytherapy has recently been modified and holds great promise for the treatment of early stage prostate cancer. Radioactive pellets or seeds of, for example, iodine-125, gold-198, palladium-103, ytterbium-169, or iridium-192, are deposited directly into the prostate through needle placement. Imaging tests, such as transrectal ultrasound, CT scans, or MRI, are used to accurately guide placement of the radioactive material. Advantageously, radiation is administered directly to the prostate with less damage to surrounding tissues, requiring a significantly smaller radiation dosage as compared to external beam radiation therapy. Furthermore, the procedure need only be performed once. Complications include a lower, yet still significant, incidence of impotence and urinary incontinence, compared to prostate removal procedures.

The radioactive seeds are placed inside thin needles, which are inserted through the skin of the perineum (area between the scrotum and anus) into the prostate. Each needle is slowly retracted with a spinning motion by a first practitioner while a plunger within the needle, and proximal of the radioactive seeds, is held stationary by a second practitioner. The plunger keeps the seeds in place during retraction of the needle, while rotation of the needle during retraction prevents jamming of the seeds while delivering the seeds in a line within the prostate.

The seeds, which are permanently implanted, give off radiation for weeks or months. Their presence causes little discomfort, and they are left in the prostate after decay of the radioactivity. For about a week following needle insertion, patients may experience pain in the perineal area, and urine may have a red-brown discoloration.

Current surgical apparatus and methods for loading the seeds into the brachytherapy needles prior to delivery are both hazardous and inefficient. Medical personnel hand-load the seeds in an alternating arrangement of seeds and spacers, thereby unnecessarily subjecting the personnel to radiation exposure. Minute seed size (e.g., 5 mm in length) compounds the problem by making the procedure slow and meticulous. Furthermore, the seeds accidentally may be dropped or misplaced during loading, thereby increasing exposure risk. Also, the seed loader may make a mistake in the packing order of seeds and spacers, potentially leading to "hot spots" and "cold spots" within a patient's prostate where the tissue is subjected to incorrect radiation dosages. Finally, the types and total number of seeds and needles used must be individualized for each patient depending on the size of the prostate and the Gleason score of the cancer, thereby increasing opportunity for error.

Attempts have been made to address various aspects of these concerns. For example, U.S. Pat. No. 4,815,449 to Horowitz describes an absorbable member with seeds spaced within the member to facilitate proper spacing during delivery. The absorbable member may be pre-formed for easy loading. While pre-forming may effectively decrease the complexity and time required to load the needles, it also impedes the physician's ability to tailor the seed spacing to a specific patient's needs. Furthermore, these absorbable members have been prone to jamming within the needle in clinical use.

U.S. Pat. No. 5,928,130 to Schmidt provides a sleeve, pre-loaded with seeds and spacers at a remote site, which may be inserted through the needle lumen. Seeds then are implanted using conventional techniques. As with the Horowitz device, the physician's ability to tailor seed spacing is limited. Furthermore, the method of loading seeds into the sleeve at the remote site is not disclosed, and presumably involves technicians at the loading site being exposed to radiation.

PCT publication WO 99/20337 to Rydell describes a gun-like radioactive seed implantation device that strips seeds one by one from a cartridge and advances them to the implantation site. The Rydell device has several drawbacks. The device is rather large and may prove intrusive in the surgical field. It increases the time required to perform surgery since seeds only may be delivered one at a time. The device also is mechanically complex and may be subject to malfunction. Finally, there is only one cartridge from which the device draws implantable materials. Thus, a packing arrangement of seeds and spacers tailored for a specific patient requires pre-loading of the cartridge, again exposing the loader to radiation.

While each of these devices may provide some benefit over the previously known apparatus and methods, none satisfactorily addresses the shortcomings of current loading techniques. In view of these drawbacks, it would be desirable to provide methods and apparatus that allow rapid seed loading both prior to and during the procedure.

It further would be desirable to provide methods and apparatus for brachytherapy seed loading that minimize radiation exposure of attendant medical personnel.

It also would be desirable to provide methods and apparatus that may be used in conjunction with standard brachytherapy needles.

It further would be desirable to provide methods and apparatus that allow tailoring of the packing arrangement of seeds and spacers to meet the needs of a specific patient.

SUMMARY OF THE INVENTION

In view of the foregoing, it is an object of the present invention to provide methods and apparatus for brachytherapy seed loading that allow rapid seed loading.

It is also an object of the present invention to provide methods and apparatus that minimize radiation exposure of attendant medical personnel.

It is another object of this invention to provide methods and apparatus that may be used in conjunction with standard brachytherapy needles.

It is a further object of the present invention to provide methods and apparatus that allow tailoring of the packing arrangement of seeds and spacers to meet the needs of a specific patient.

These and other objects of the present invention are accomplished by providing methods and apparatus for brachytherapy seed loading comprising a apparatus with at least two detachable loading cartridges. One cartridge dispenses radioactive seeds; the other dispenses spacers. When used in conjunction with a standard brachytherapy needle and plunger, the present invention allows quick and easy loading of tailored seed delivery profiles, and reduces radiation exposure of medical personnel.

In a preferred embodiment, the distal end of the tube lumen is in communication with a lumen of the brachytherapy needle. The plunger is inserted in the proximal end of the tube lumen. The loading cartridges are in communication with the tube lumen, and the plunger may be advanced to controllably dislodge seeds or spacers from the cartridges, which in this embodiment are gravity-fed into the needle lumen. In an alternative embodiment, a specialized plunger may be used in place of the standard brachytherapy plunger to strip selectively seeds/spacers from the cartridges regardless of orientation.

In an alternative embodiment, the cartridges dispense seeds/spacers into loading chambers with reciprocating stylets. The stylets are selectively actuated to push seeds or spacers from the loading chambers into a collection chamber, and subsequently into the needle lumen. The loading chambers may be pre-loaded or communicate with bulk hoppers that provide a sequence of seeds or spacers.

Methods of using the present invention also are provided. In addition, methods and apparatus are provided for retaining the seeds and spacers in alignment prior to loading into the needles.

BRIEF DESCRIPTION OF THE DRAWINGS

Additional objects and advantages of the invention will be apparent from the following description, the accompanying drawings and the appended claims, in which:

FIGS. 6A and 6B are, respectively, an isometric and a top view of an embodiment of the present invention;

DETAILED DESCRIPTION OF THE INVENTION

The present invention provides methods and apparatus for loading radioactive seeds into brachytherapy needles. More particularly, the present invention provides a tube with two loading cartridges filled respectively with seeds and spacers. The seeds and spacers controllably are stripped from the cartridges and loaded into the needles.

Figure 1:
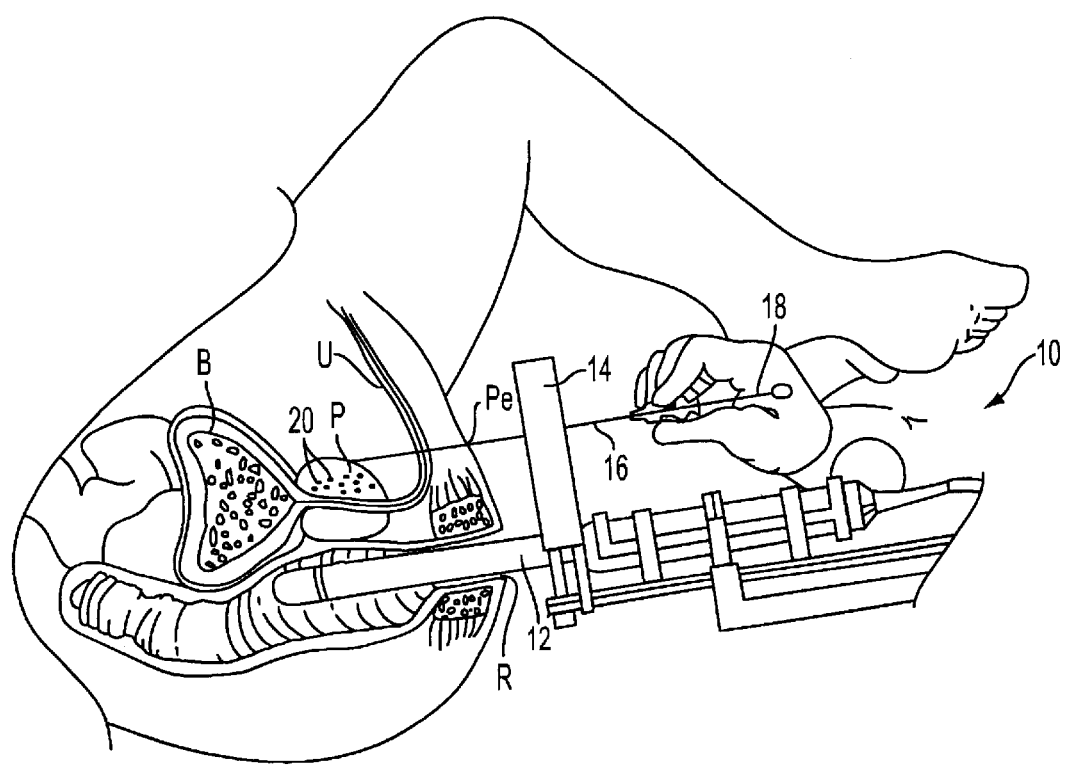
FIG. 1 is a schematic view of a prior art method of performing brachytherapy.

Referring now to FIG. 1, the prior art method of performing brachytherapy is described. The method and apparatus are as taught by Peter Grimm, DO, in a pamphlet entitled, "Ultrasound Guided Implantation of the Prostate: A Practical Review Course." Brachytherapy apparatus 10 comprises transrectal ultrasound probe 12, guide block 14, needle 16, plunger 18, and radioactive seeds 20. Ultrasound probe 12 is advanced through a patient's rectum R to facilitate imaging of the patient's prostate P. Prostate P surrounds the urethra U and is just proximal of the bladder B. Needle 16, loaded with seeds 20 and plunger 18, is advanced through the patient's perineum Pe into prostate P, where needle 16 is retracted and seeds 20 are delivered to the patient. Radioactive seeds 20 and spacers 22 (see FIG. 2) are commonly loaded into needles 16 by hand, the drawbacks of which are described hereinabove.

Figure 2:
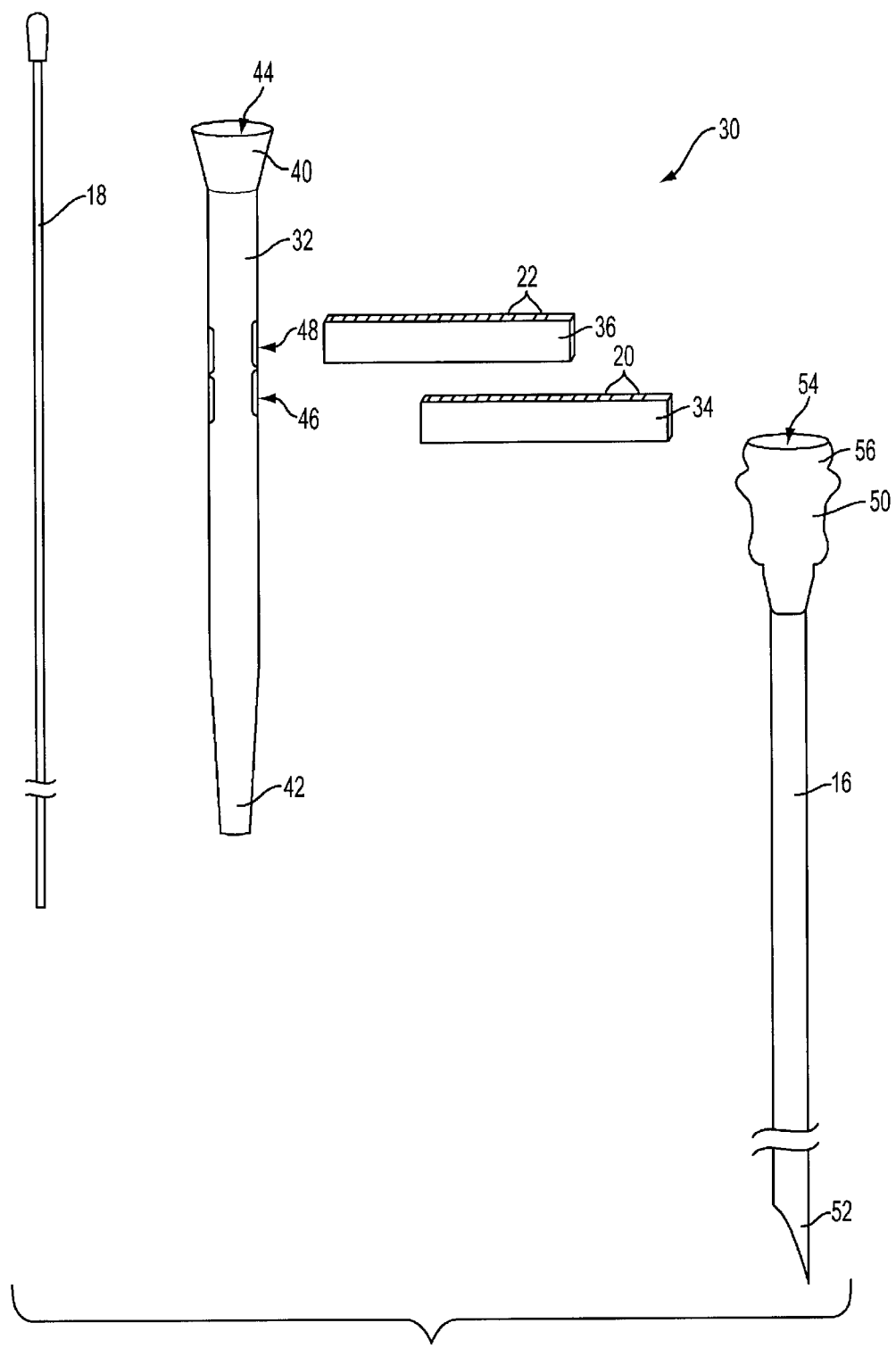
FIG. 2 is an exploded side view of apparatus constructed in accordance with the present invention.

With reference to FIG. 2, apparatus constructed in accordance with the present invention for loading seeds into needles is described. Apparatus 30 comprises loading tube 32, radioactive seed cartridge 34 containing seeds 20, and spacer cartridge 36 containing spacers 22. Apparatus 30 may be used in conjunction with standard brachytherapy needle 16 and plunger 18 of FIG. 1. Loading tube 32 comprises enlarged proximal end 40, tapered distal end 42, and lumen 44 extending therebetween. It further comprises transverse slots 46 and 48 configured to slidably receive cartridges 34 and 36.

Needle 16 comprises proximal end 50, sharpened distal end 52, and lumen 54 extending therebetween. Proximal end 50 comprises hub 56 that facilitates manipulation of the needle. The opening at the distal tip of needle 16 is initially filled with bone wax that melts when placed inside the body. The needle lumen is filled, in an alternating pattern, with seeds 20 and spacers 22. For this purpose, tapered distal end 42 of loading tube 32 is configured to be received in lumen 54 of needle 16, which extends through hub 56. Likewise, plunger 18 is configured to be received in enlarged proximal end 40 of loading tube 32.

Figure 3:
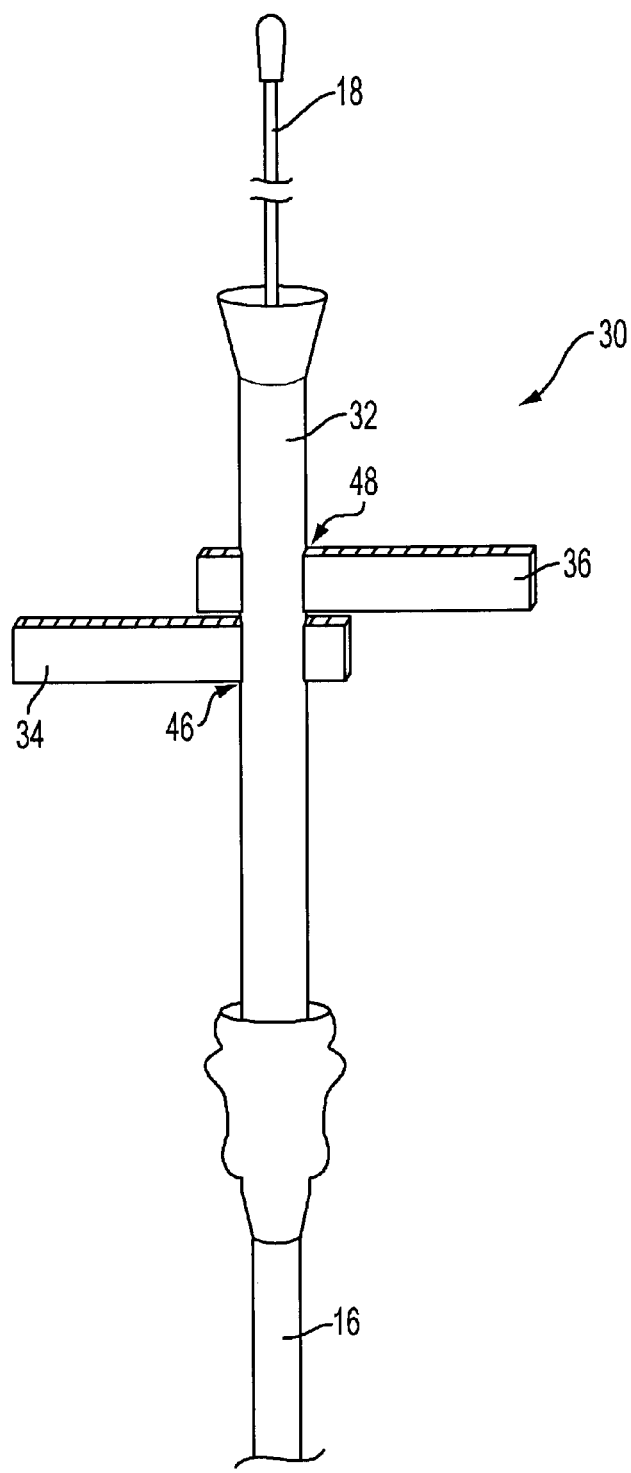
FIG. 3 is an assembled side view of the apparatus of FIG. 2.
Figure 4:
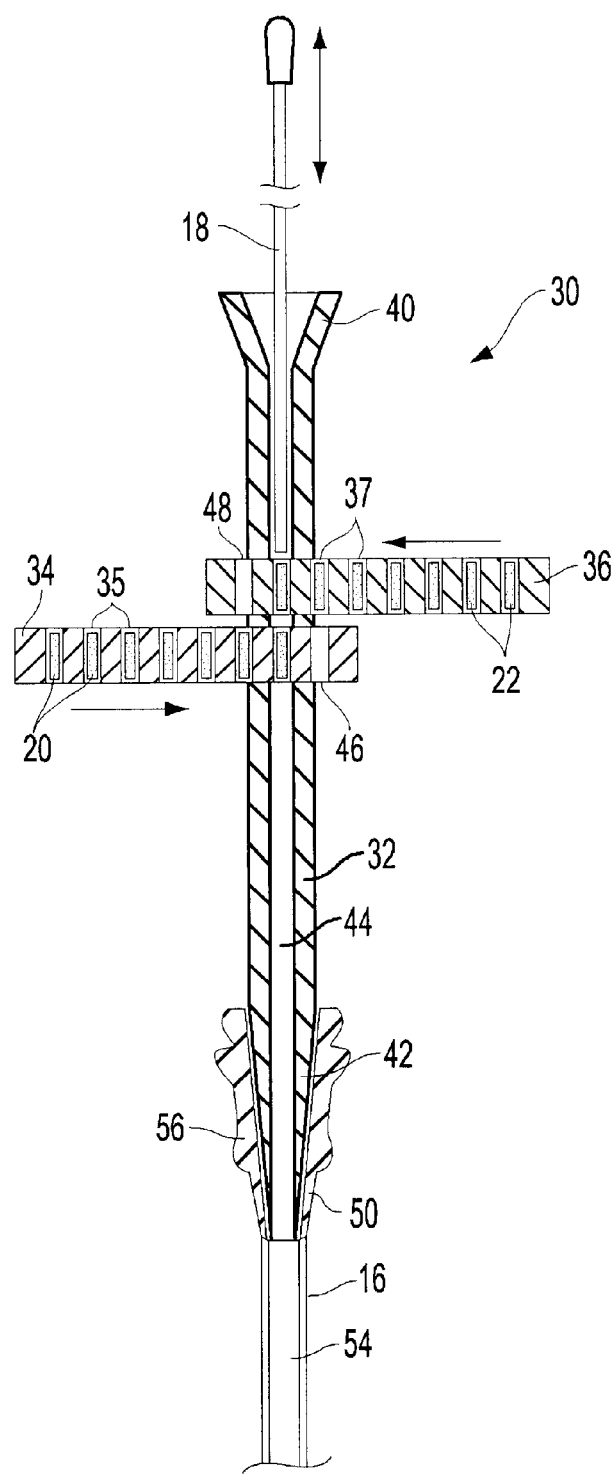
FIG. 4 is a cross-sectional view of the apparatus of FIGS. 2 and 3.

With respect to FIGS. 3 and 4, the apparatus of FIG. 2 is shown assembled for use loading needle 16. Cartridges 34 and 36 are slidably disposed within transverse slots 46 and 48, tube 32 is received within needle 16, and plunger 18 is disposed in tube 32.

Cartridges 34 and 36 each comprise a plurality of chambers 35 and 37, respectively, which are configured to receive seeds 20 and spacers 22, respectively. The seeds and spacers may, for example, be loaded into the chambers by remotely operated machines, so that radiation exposure is mitigated. Alternatively, the seeds or spacers may be press-fit into chambers 35 and 37, or retained within chambers 35 and 37, for example, by bone wax. Cartridge 34 preferably also comprises a shielding material, such as lead. As a further alternative, cartridges 34 and 36 may comprise a transparent or translucent material to facilitate determination of whether the chambers are full or empty. The cartridges may be configured such that chambers 35 or 37 are arranged in a linear fashion. Additionally, cartridges 34 and 36 may have any one of a variety of alternative structures described hereinafter with respect to FIGS. 5A–5D, depending upon the intended context for use of the apparatus.

A method of using apparatus 30 is now described. Tapered distal end 42 of loading tube 32 is received by lumen 54 in hub 56 of needle 16, plunger 18 is disposed in enlarged proximal end 40 of loading tube 32, and the opening at the distal tip of needle 16 is filled with bone wax. Cartridges 34 and 36 translate within slots 46 and 48 until first chamber 35 and first chamber 37 align with lumen 44 of loading tube 32. The distal end of plunger 18 is advanced from the proximal to the distal end of lumen 44, thereby passing through chamber 35 and chamber 37 aligned with lumen 44.

If seed 20 or spacer 22 is contained, respectively, in chamber 35 or chamber 37 aligned with lumen 44, it is forced out of the chamber by distal advancement of plunger 18 and is gravity-fed through lumen 44 into lumen 54 of needle 16. If no seed or spacer is in a chamber aligned with the lumen, plunger 18 passes unencumbered through that chamber. Once a chamber has been emptied, the cartridges may be advanced through slots 46 and 48 to align subsequent filled chambers with lumen 44.

Thus, a medical practitioner can load needle 16 with a tailored packing arrangement of seeds 20 and spacers 22 by selectively aligning filled or empty chambers 35 and 37 with lumen 44 of loading tube 32, and distally advancing plunger 18 through the chambers. Alternatively, the positioning of cartridges 34 and 36, as well as actuation of plunger 18, may be controlled by automated means, such as are known in the art. The funnel shape of tapered end 42 is expected to prevent the jamming commonly seen at the interface of hub 56 and needle 16 during hand loading.

Alternatively, the chambers may be configured so that if seed 20 or spacer 22 is contained, respectively, in chamber 35 or chamber 37 aligned with lumen 44, it exits the chamber and enters lumen 44 by the force of gravity, without the need for plunger 18. Plunger 18 may assist with seeds or spacers that have become stuck in the chamber, the loading tube, or the needle. Once a chamber has been emptied, the cartridges may be advanced through slots 46 and 48 to align subsequent filled chambers with lumen 44.

Alternatively, the invention may comprise a single cartridge containing seeds and spacers pre-loaded in the desired order, such that advancing the single cartridge will discharge seeds and spacers into lumen 44 and subsequent lumen 54 of needle 16 in the same predetermined order.

Referring now to FIGS. 5A–5D, an alternative seed or spacer cartridge comprises a single unpartitioned chamber with aperture 38 at one end. The chamber may contain either plurality of seeds 20 or plurality of spacers 22. The seeds and spacers may move freely within their respective cartridges, but are biased towards the aperture. The biasing force may be imposed by compressed spring 39 contained within the cartridge, as in cartridge 34a depicted in FIG. 5A; by making the interior surface of the cartridge in the form of an inclined ramp, as in cartridge 34b depicted in FIG. 5B, so that weight 41 biases the seeds or spacers toward the aperture; by directional ratchet 43, as in cartridge 34c depicted in FIG. 5C; or by combinations thereof. The cartridge may further comprise window 45 disposed exteriorly thereon, as in cartridge 34d depicted in FIG. 5D, so that the user may view the seeds or spacers contained therein. Indicia 47 may be disposed about window 45, such that the quantity of seeds or spacers contained within the cartridge may be determined by correspondence of the visible amount of seeds or spacers to the indicia.

When these cartridges are assembled within the transverse slots of loading tube 32, apertures 38 of the cartridges align with lumen 44 of loading tube 32. By advancing plunger 18, or by controllably opening the aperture, a seed or spacer may enter lumen 44 from the cartridge via the aperture.

Figure 5A:
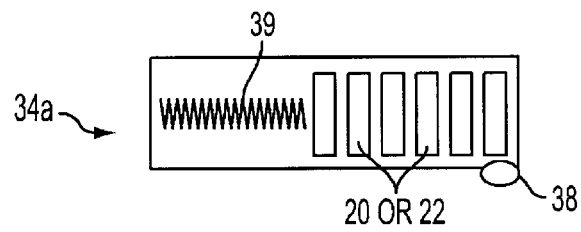
FIGS. 5A–5F are views of alternative cartridges to be used in conjunction with the apparatus of the present invention.
Figure 5B:
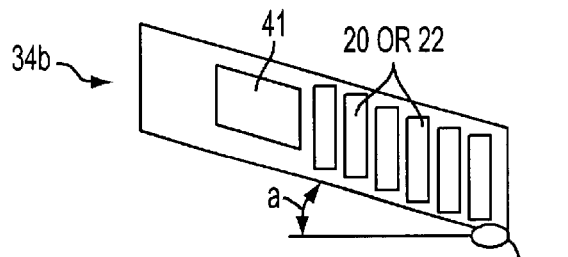
Figure 5C:
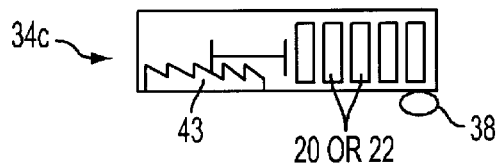
Figure 5D:
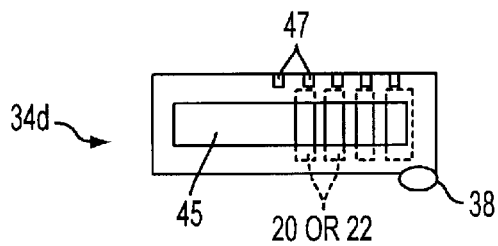
Figure 5E:
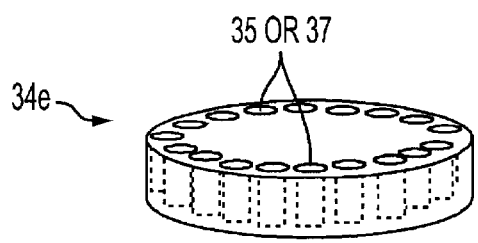

As a further alternative embodiment, an alternative cartridge may conform to an approximate cylindrical shape such as cartridge 34e depicted in FIG. 5E, with chambers 35 or 37 circumferentially arranged in a circular arrangement. In this embodiment the cartridges are rotated to bring the desired seed or spacer into alignment with the loading chamber.

Figure 5F:
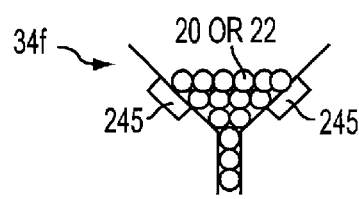

As a yet further alternative, seeds 20 or spacers 22 may be made available from bulk quantities using vibrating hoppers. As shown in FIG. 5F, the cartridges may further comprise vertical hoppers 34f that continuously funnel a sequence of seeds or spacers into the loading chamber by gravity. Vibrating mechanism 245 may be associated with each hopper to reduce jamming. This embodiment would have the advantage of rapid and simplified filling with seeds or spacers.

Figure 6B:
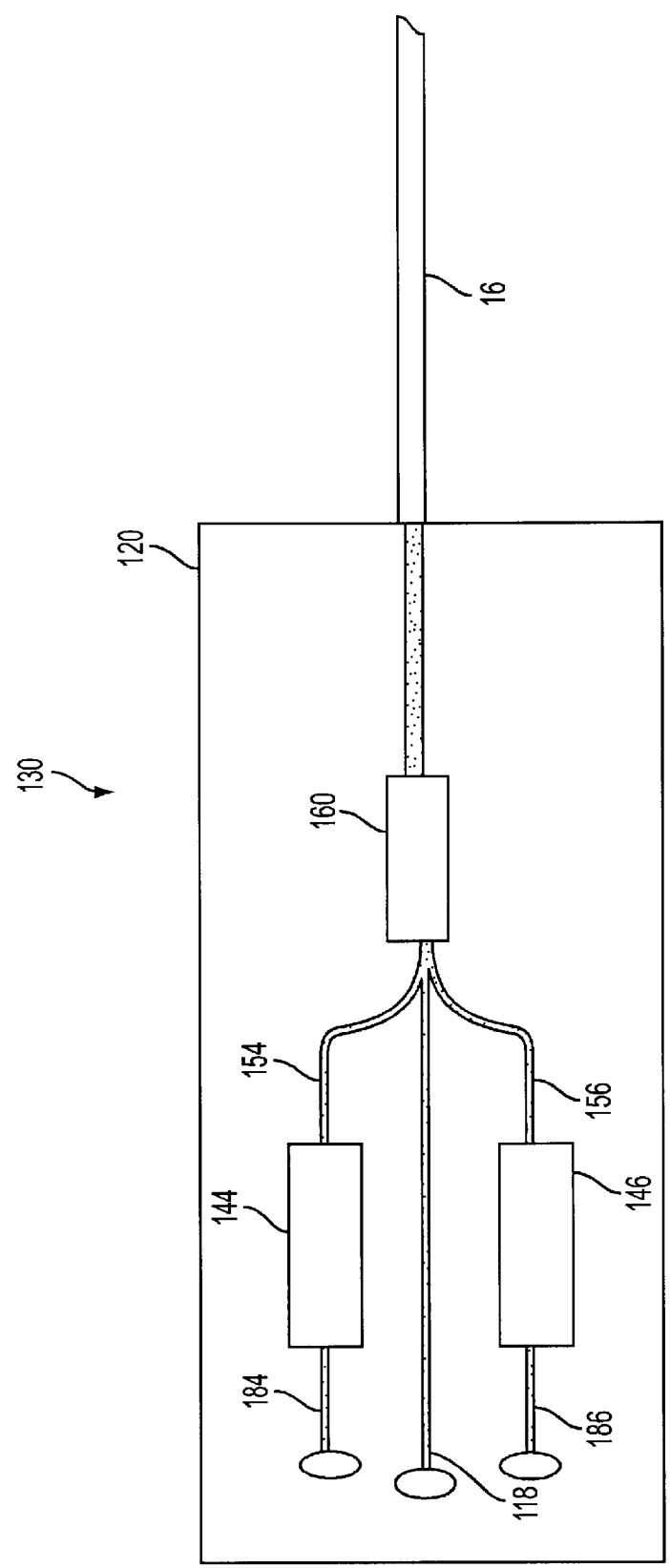

With respect to FIGS. 6A and 6B, a preferred apparatus for tailoring the radioactive seed spacing and for loading a predetermined arrangement of seeds and spacers into a standard brachytherapy needle is described. Apparatus 130 comprises main body 120 to which standard brachytherapy needle 16 may be removably coupled, collection chamber 160 and loading plunger 118. Collection chamber 160 is disposed near the distal end of main body 120 but proximal to the attachment point of brachytherapy needle 16. Collection chamber 160 may contain the predetermined arrangement of radioactive seeds and spacers prior to loading into brachytherapy needle 16. Loading plunger 118 is disposed proximal to and aligned with collection chamber 160 and needle 16, such that distal advancement of the plunger passes its distal end through collection chamber 160, pushing the contents therein into needle 16.

Collection chamber 160 also may be configured to allow the user to confirm the presence and the order of the seeds and spacers arranged therein. Collection chamber 160 also may incorporate shielding material to provide radiation protection, such as lead, glass with graphite, steel, water or aluminum. Alternatively, or in addition, the collection chamber may provide a removable/slidable cover for the user to remove or to manipulate the contents therein. Collection chamber 160 also may incorporate a device for measuring the radiation of seeds contained therein, such as a Geiger counter, scintillation counter, or the like.

To arrange the desired seeds and spacers in collection chamber 160, apparatus 130 further comprises at least one loading stylet 184, 186 and at least one cartridge (containing seeds and/or spacers) 134, 136. These components are disposed at a position proximal to the collection chamber 160. With the preferred embodiment of FIGS. 6A and 6B, apparatus 130 includes first loading chamber 144 and second loading chamber 146, wherein distal ends of loading chambers 144 and 146 are connected to a proximal end of collection chamber 160 by conduits 154 and 156, respectively. These conduits merge into a single conduit prior to entering the collection chamber. This embodiment further comprises loading stylets 184 and 186 proximally disposed to loading chambers 144 and 146, respectively. Each loading stylet may be moved independently in a reciprocating motion. Therefore, the distal end of each stylet may be advanced towards the distal end or retracted towards the proximal end. The length and the range of movement of loading stylets 184 and 186 are configured such that the stylets may travel from at least the distal end of collection chamber 160 to the proximal end of their respective loading chambers. Alternatively, the stylets may advance or retract by use of a telescoping mechanism. Furthermore, it is also preferred that the stylets be sufficiently flexible to adapt to deviations from linearity during advancement and retraction.

From its most proximal position, first loading stylet 184 is advanced distally, the stylet passes through loading chamber 144, pushing out any seeds and/or spacers contained therein. Continued distal advancement of the stylet pushes the seeds and/or the spacers to the distal end of collection chamber 160 via conduit 154. Similarly, second loading stylet 186 is associated with second loading chamber 146 and second conduit 156, and is configured and functions in a corresponding manner.

The movement of the loading stylets may be controlled by a mechanism associated with each stylet. These mechanisms may include a means to mechanically or electrically transmit motion to each stylet, such a handle, button, knob, lever, spring, solenoid or switch. These mechanisms may be actuated by a user or by automated means.

Seeds and spacers are provided within each loading chamber by an associated cartridge. In the preferred embodiment, first cartridge 134 is associated with first loading chamber 144, the cartridge comprising one or more stacks of seeds or spacers. Second cartridge 136 is similarly associated with second loading chamber 146, and also comprises one or more stacks of seeds or spacers. A cartridge, when assembled with its respective loading chamber, is configured to deposit a single seed or spacer from each stack into the loading chamber. Following displacement of the seed or spacer from the loading chamber by the loading stylet, a new seed and/or spacer from the associated cartridge will be deposited within the loading chamber.

Referring now to FIGS. 7A–7E, the present invention may incorporate apparatus for wrapping an arrangement of seeds and spacers in a bio-compatible or bio-absorbable material prior to loading into the brachytherapy needle. Advantageously, the wrapping preserves the integrity and order of the seed and spacer arrangement during loading into the brachytherapy needle and during subsequent implantation within the patient. In addition, wrapping may obviate the need for spacers by maintaining the relative spacing of the seeds. The seeds and spacers may be wrapped while contained within the collection chamber, or the seeds and spacers (if present) may be moved to another chamber to perform the wrapping.

Figure 7A:
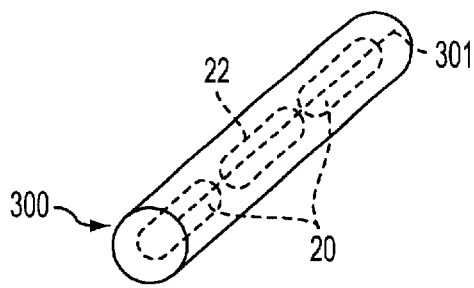
FIGS. 7A–7I depict alternative methods for wrapping a series of seeds and spacers after arrangement in the collection chamber.
Figure 7B:
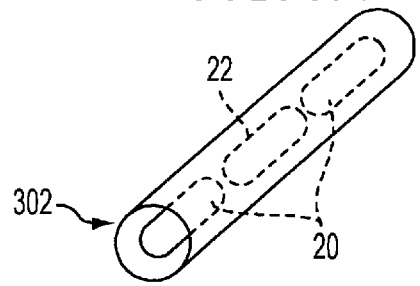
Figure 7C:
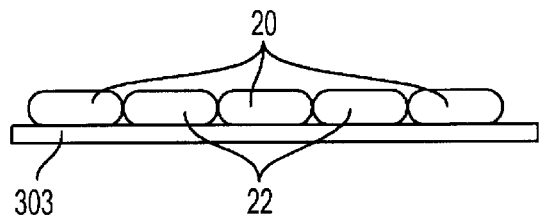
Figure 7D:
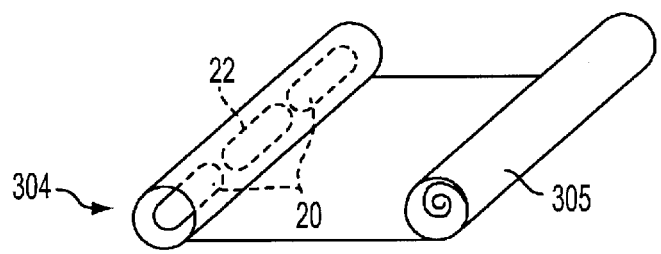
Figure 7E:
Figure 7F:
Figure 7G:
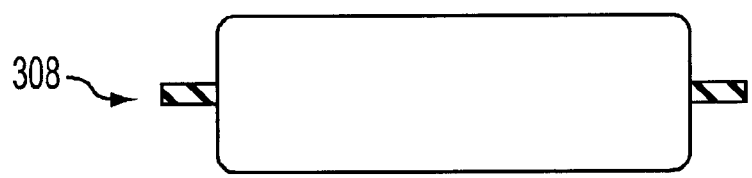
Figure 7H:
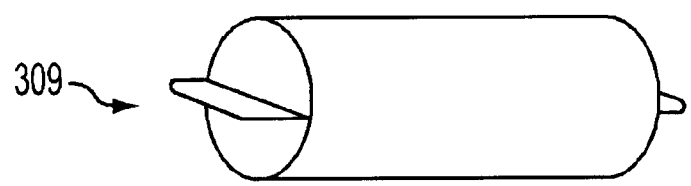
Figure 7I:
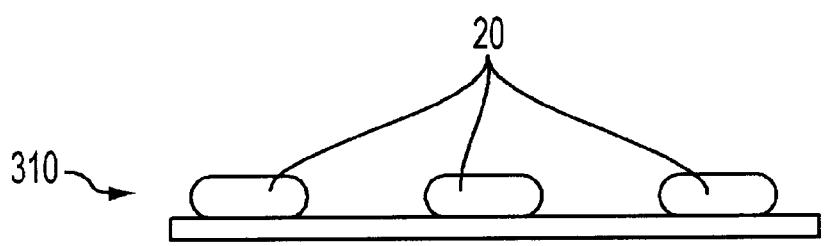

In FIG. 7A, the wrapping comprises a tube or sleeve 300 with longitudinal slit 301. In this embodiment, the tube or sleeve closes around seeds 20 and spacers 22, thereby enclosing the seeds and spacers within. In FIG. 7B, the seeds and spacers are press-fit into tube 302 from one end. In FIG. 7C, the seeds and spacers include features that engage rod or tube 303. Rod or tube 303 may enclose the seeds and spacers, or the seeds and spacers may be disposed on its outer surface. In the embodiment FIG. 7D, roll of wrapping material 305 is associated with the wrapping chamber, and dispenses a suitable amount of wrapper 304 to surround the seeds and spacers. In FIG. 7E, the seeds and spacers are fitted into articulated coil 306. The foregoing wrappers may further immobilize the seeds and the spacers contained within by adhesives or by heat-shrinking. The wrapped seeds and spacers also may be further immobilized by closing or narrowing of the proximal and distal ends of the wrapper, such as by forming a retaining member, twisting, or sealing the ends, thereby more securely retaining the contents therein. These wrappers 307, 308, and 309 are depicted in FIGS. 7F–7H, respectively. Moreover, all of the embodiments of FIGS. 7A–7H may be used without spacers. In this case, the seeds are arranged in the predetermined manner, separated by gaps rather than physical spacers as depicted in FIG. 7I. Once arranged in this manner, wrapper 304 may be used to immobilize the seeds in the desired arrangement for loading into the needle and implantation.

Referring again to FIG. 6A, a method of using the embodiment of apparatus 130 is now described. In this example, first cartridge 134 comprises a stack of spacers and a stack of seeds, and second cartridge 136 comprises a single stack of spacers. It is understood that this particular configuration is exemplary only, and one skilled in the art may use an alternate configuration of seeds or spacers most appropriate for a desired arrangement to be loaded into the brachytherapy needle.

The cartridges are assembled within their respective loading chambers as described hereinabove. A single seed 20 and a single spacer 22 are deposited in first loading chamber 144 from first cartridge 134. A single spacer 22 is then deposited in second loading chamber 146 from the stack of spacers within second cartridge 136.

First loading stylet 184 is advanced distally to push seed 20 and spacer 22 as an ordered pair from first loading chamber 144 into first conduit 154. Further advancement of first stylet 184 will push seed 20 and spacer 22 to the distal end of collection chamber 160. Loading stylet 184 is then proximally retracted, leaving seed 20 and spacer 22 in collection chamber 160. The path from loading chamber 144 to collection chamber 160 is configured to maintain the order of the seed and spacer during transit. After retraction of the stylet past first loading chamber 144, a new seed 20 and spacer 22 may be deposited within first loading chamber 144 from first cartridge 134. Repeating the advancement and retraction of first loading stylet 184 in the aforementioned manner assembles an arrangement of alternating seeds and spacers within collection chamber 160. If the insertion of additional spacers is desired during the assembly, second loading stylet 186 may be advanced distally to push a spacer 22 from second loading chamber 146 into second conduit 156, and subsequently into collection chamber 160. This spacer 22 is deposited proximal to the last seed and spacer pair previously deposited, thereby adding an additional spacer.

Once a desired arrangement of seeds and spacers is assembled within collection chamber 160, this arrangement may be inspected, corrected, or wrapped in the manner described hereinabove. To load distally attached brachytherapy needle 16 with the seeds and spacers, loading plunger 118 is advanced distally through collection chamber 160 until its distal end reaches at least the proximal end of receiving needle 16. This advancement pushes the ordered linear arrangement of seeds and spacers from collection chamber 160 into brachytherapy needle 16. Loaded brachytherapy needle 16 may then be removed in preparation for therapeutic implantation.

The assembly and loading procedure described hereinabove may be performed under the control of a user such as a medical practitioner. Alternatively, said assembly and loading may be performed by automated means, such as are known in the art.

Figure 8A:
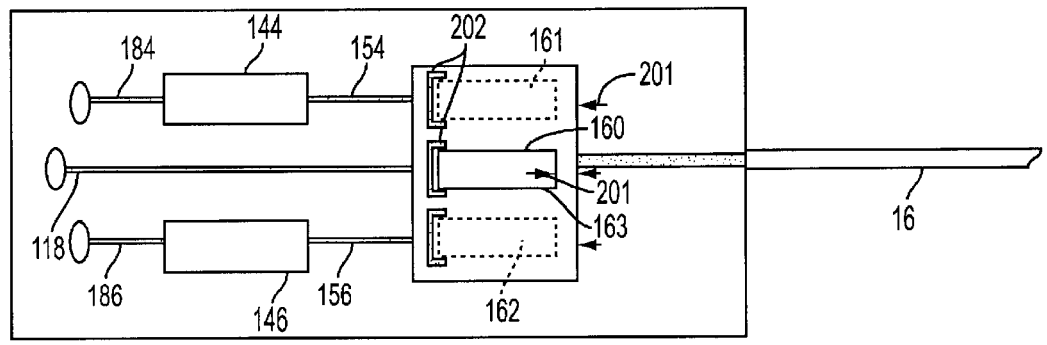
FIG. 8A is a top view of an embodiment comprising a movable collection chamber.

Referring now to FIG. 8A, an alternative embodiment of the invention is described. In this embodiment, conduits 154 and 156 do not converge towards collection chamber 160. Instead, the collection chamber may move along an axis approximately perpendicular to the main axis of the apparatus. This movement thereby allows collection chamber 160 to be positioned in approximate alignment with a specific stylet, loading chamber, and conduit when receiving seeds and/or spacers from that loading chamber. Thus, for example, collection chamber 160 is moved to position 161 and 162 to receive seeds or spacers from loading chamber 144 and 146, respectively. Indicia 201 may be provided on the apparatus and the collection chamber to ensure correct alignment in the manner described. Guide stops 202 also may be provided to limit the available positions of the collection chamber, thereby ensuring correct alignment. Once the desired arrangement of seeds and spacers is assembled within collection chamber 160, the collection chamber is moved to position 163 where it is in approximate alignment with plunger 118 and brachytherapy needle 16.

Figure 8B:
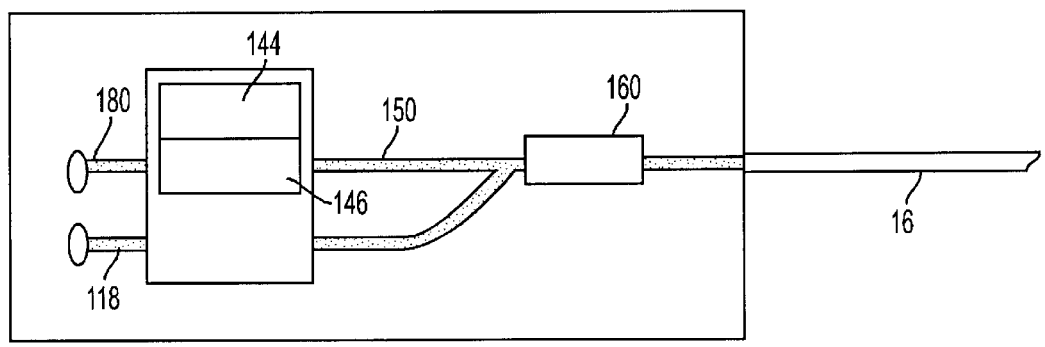
FIG. 8B is a top view of the alternative embodiment comprising movable loading chambers.

Yet another alternative embodiment is shown in FIG. 8B, in which loading chambers 144 and 146 move along an perpendicular axis. In this embodiment, a specific loading chamber may be aligned with collection chamber 160 when transferring seeds and/or spacers from that loading chamber to collection chamber 160. In a manner similar to that described in the embodiment depicted in FIG. 8A, indicia and guide stops may be provided to ensure correct alignment of the loading chambers in each position. This embodiment further may comprise a loading stylet associated with each movable loading chamber, or alternatively, single loading stylet 180 may remain fixed and approximately aligned with collection chamber 160. The loading of brachytherapy needle 16 may require that the loading chambers be moved to allow unhindered advance of loading plunger 118 to collection chamber 160. Both of the aforementioned embodiments may provide the advantage of requiring shorter conduits and stylets, with the further advantage of decreasing the possibility of jamming seeds or spacers during transit.

Figure 9:
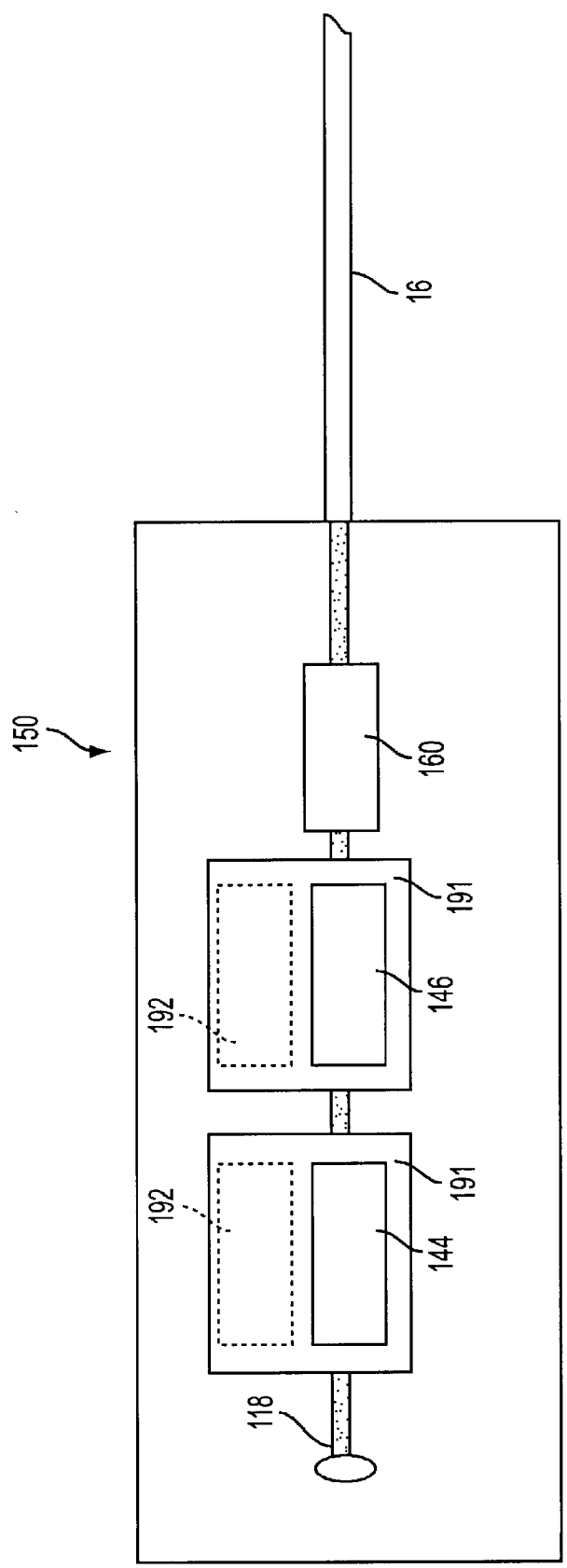
FIG. 9 is a view of an alternate arrangement of the loading chambers.

With respect to FIG. 9, another embodiment of apparatus 130 comprises one or more perpendicularly and independently movable loading chambers. Each loading chamber is associated with a cartridge containing seeds or spacers. The loading chambers are disposed serially on the apparatus proximal to collection chamber 160 and distal to loading stylet 180. Each of the loading chambers are movable between first position 191 and second position 192. When a loading chamber is in first position 191, loading stylet 180, the loading chamber and collection chamber 160 become aligned approximately along a single axis, such that the distal advancement of loading stylet 180 passes through the loading chamber and into subsequent collection chamber 160, distally pushing seeds and/or spacers contained therein. If more than one loading chamber is in first position 191 and aligned in the aforementioned manner, the distal advancement of stylet 180 will pass through each loading chamber in series. If a loading chamber is moved into second position 192, distal advancement of the loading stylet will bypass that loading chamber and hence any seed or spacer contained therein. In a manner similar to that described in the embodiment depicted in FIG. 8A, indicia and guide stops may be provided to ensure correct alignment of the loading chambers in each position. The apparatus may further comprise additional cartridges, either in series or in parallel, to provide greater flexibility when assembling a desired arrangement of seeds and spacers. Once the desired arrangement of seeds and spacers is assembled within collection chamber 160, the loading chambers may be moved to second position 192 so that stylet 180 may advance or telescope distally, pushing the ordered arrangement of seeds and spacers from collection chamber 160 into brachytherapy needle 16.

Figure 10A:
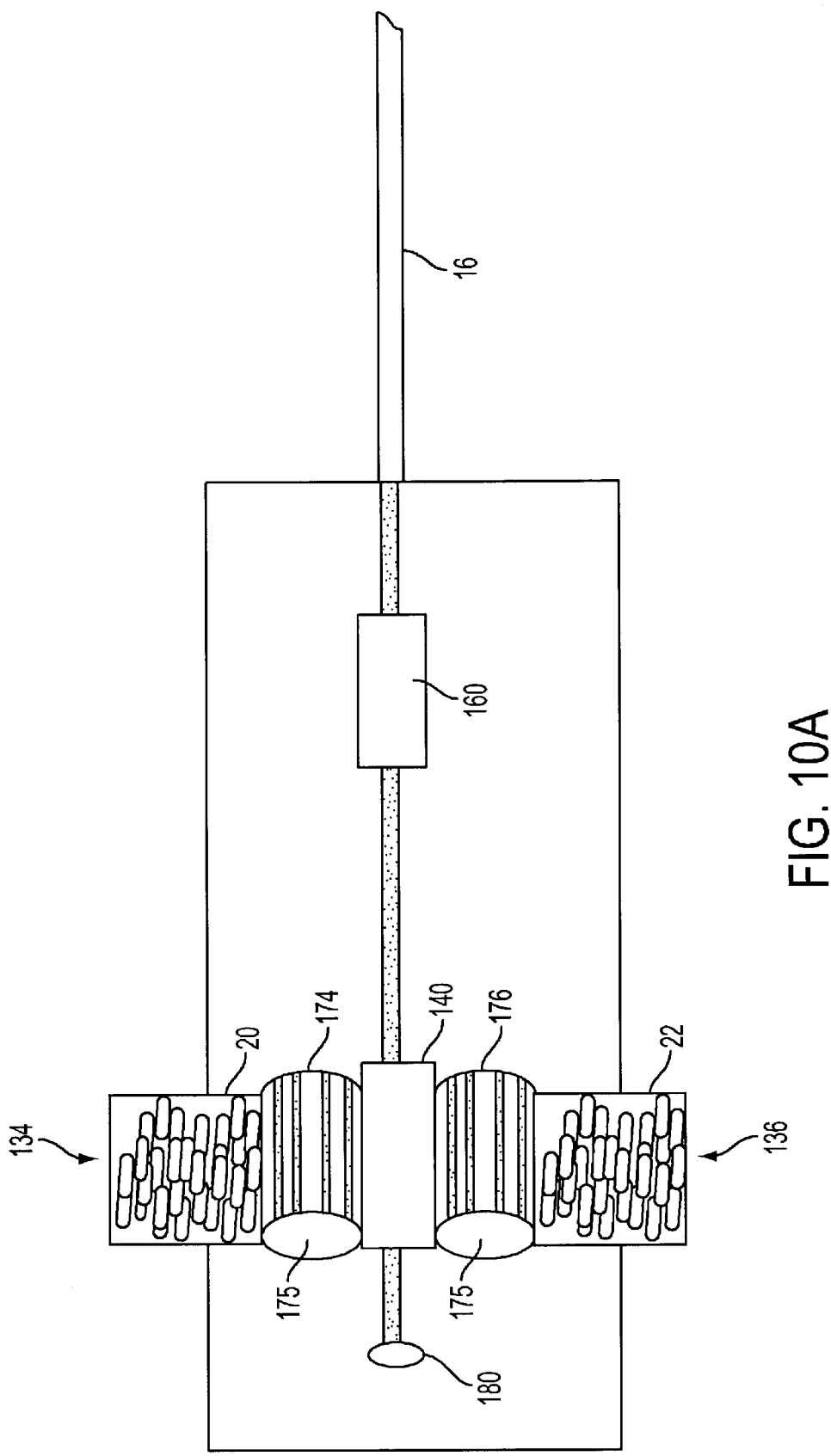
FIGS. 10A and 10B are, respectively, top and a cross-sectional view of the feed drum embodiment of the present invention.
Figure 10B:
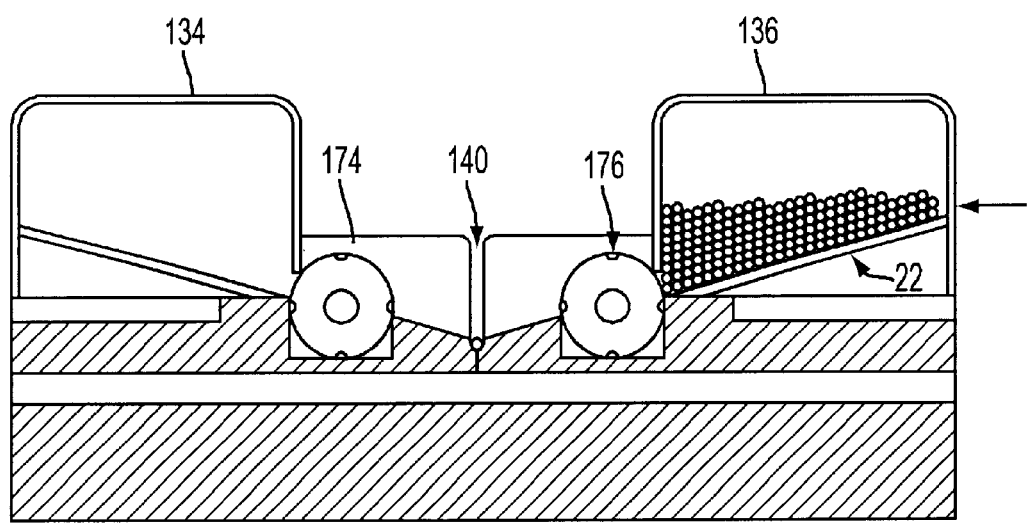

With respect to FIGS. 10A and 10B, a further alternative embodiment of the apparatus is described. The apparatus comprises loading stylet 180, loading chamber 140, collection chamber 160, and attached standard brachytherapy needle 16, all approximately aligned along a single axis. Distal advancement of loading stylet 180 passes through the loading chamber, the collection chamber, and needle 16, thereby pushing distally the contents therein.

The apparatus further comprises first hopper 134 disposed on one side of loading chamber 140, and second hopper 136 disposed on the other side. For the purposes of illustration, first hopper 134 and second hopper 136 contain, respectively, a plurality of seeds 20 and a plurality of spacers 22. The hoppers are configured for convenient loading of seeds or spacers, thereby minimizing user manipulation of radioactive seeds.

First feed drum 174 is disposed between first hopper 134 and loading chamber 140. First feed drum 174 includes a plurality of grooves 175 embedded on its cylindrical surface, and a knob for rotating the feed drum around its central axis. The knob and feed drum may be ratcheted to restrict rotation of the drum to a single angular direction in discrete intervals. To deliver a single seed 20 from first hopper 134 to loading chamber 140, feed drum 174 is rotated such that embedded groove 175 engages seed 20 from hopper 134. The feed drum is rotated further, conveying the engaged seed 20 to loading chamber 140 and depositing it therein. Once seed 20 is deposited within loading chamber 140, loading stylet 180 may be distally advanced to push seed 20 into the collection chamber. Second feed drum 176 is disposed between second hopper 136 and loading chamber 140. The second feed drum comprises features and functions analogous to the first feed drum, and thus may deliver spacer 22 into loading chamber 140 in a similar manner. Therefore, a predetermined arrangement of seeds and spacers may be assembled by delivering seeds or spacers from hoppers 134 and 136 into loading chamber 140. Once the desired arrangement of seeds and spacers is assembled within collection chamber 160, stylet 180 may be advanced to push the arrangement from collection chamber 160 into brachytherapy needle 16.

The loading procedures described hereinabove is expected to be efficient and reduce the length of time required to load brachytherapy needles, even when loading a tailored arrangement of seeds and spacers. In addition, the radiation exposure of medical personnel responsible for loading the needles is expected to be reduced.

Although particular embodiments of the present invention have been described above in detail, it will be understood that this description is merely for purposes of illustration. Specific features of the invention are shown in some drawings and not in others; this is for convenience only, and any feature may be combined with another in accordance with the invention. Further variations will be apparent to one skilled in the art in light of this disclosure, for example, the apparatus may comprise a specialized plunger instead of being used in conjunction with a standard brachytherapy plunger, and all such variations are intended to fall within the scope of the appended claims.

What is claimed is:

1. Apparatus for loading therapeutic materials into a brachytherapy needle comprising:
    a collection chamber having a distal end configured to communicate with a brachytherapy needle;
    a first cartridge comprising a plurality of seeds, the first cartridge disposed in communication with the collection chamber;
    a second cartridge comprising a plurality of spacers, the second cartridge disposed in communication with the collection chamber; and
    first and second loading chambers, each one of the first and second loading chambers having an end in communication with the collection chamber and a second end configured to receive seeds and spacers from the first and second loading cartridges, respectively.

2. The apparatus of claim 1 further comprising a first loading stylet disposed for reciprocation through the first loading chamber.

3. The apparatus of claim 2 further comprising a second loading stylet disposed for reciprocation through the second loading chamber.

4. The apparatus of claim 3 further comprising means for controlling reciprocation of the first and second stylets.

5. The apparatus of claim 1 wherein the collection chamber is adapted to move perpendicularly to selectively align with the first and second loading chambers.

6. The apparatus of claim 5 further comprising means for ensuring correct alignment of the collection chamber with the first and second loading chambers.

7. The apparatus of claim 1 wherein the first and second loading chambers are adapted to move perpendicularly to selectively align with the collection chamber.

8. The apparatus of claim 7 further comprising means for ensuring correct alignment of the first and second loading chambers with the collection chamber.

9. The apparatus of claim 1 wherein the first loading chamber and the second loading chamber are deposited in tandem and proximal to the collection chamber.

10. The apparatus of claim 9 further comprising a loading stylet proximal and disposed for reciprocation through first and the second loading chambers.

11. The apparatus of claim 10 wherein the first and second loading chambers are further configured to be independently moved out of alignment with the loading stylet and the collection chamber.

12. The apparatus of claim 11 further comprising means for ensuring correct alignment of the first and second loading chambers to the loading stylet and the collection chamber.

13. The apparatus of claim 1 further comprising a third loading chamber and a third cartridge containing a plurality of radioactive seeds or a plurality of spacers, the third cartridge disposed in communication with the third loading chamber, and interposed between the loading stylet and collection chamber.

14. The apparatus of claim 13 wherein the loading stylet and collection chamber are configured to align with any of the first, second or third loading chambers.

15. The apparatus of claim 14 further comprising means for ensuring correct alignment of the stylet and the collection chamber with the first, second or third loading chambers.

16. The apparatus of claim 1 wherein the seeds or spacers contained within the first and second cartridges are urged towards the first and second loading chambers by spring force.

17. The apparatus of claim 1 wherein the seeds or spacers contained within the first and second cartridges are urged towards the first and second loading chambers by gravity.

18. The apparatus of claim 1 wherein the seeds or spacers contained within the first and second cartridges are urged towards the first and second loading chambers by weighted body.

19. The apparatus of claim 1 wherein the seeds or spacers contained within the first and second cartridges are urged towards the first and second loading chambers by directional ratchet.

20. The apparatus of claim 1 wherein the seeds or spacers contained within the first and second cartridges are delivered to the first and second loading chambers by rotating feed drums.

21. Apparatus for loading therapeutic materials into a brachytherapy needle comprising:
    a collection chamber having a distal end configured to communicate with a brachytherapy needle;
    a first cartridge comprising a plurality of seeds, the first cartridge disposed in communication with the collection chamber; and
    a second cartridge comprising a plurality of spacers, the second cartridge disposed in communication with the collection chamber,
    wherein the first and second cartridges are cylindrical in shape, with the plurality of seeds or spacers arranged circumferentially therein.

22. Apparatus for loading therapeutic materials into a brachytherapy needle comprising:
    a collection chamber having a distal end configured to communicate with a brachytherapy needle;
    a first cartridge comprising a plurality of seeds, the first cartridge disposed in communication with the collection chamber; and
    a second cartridge comprising a plurality of spacers, the second cartridge disposed in communication with the collection chamber,
    wherein the first and second cartridges further comprise means for viewing quantity of seeds or spacers contained therein.

23. Apparatus for loading therapeutic materials into a brachytherapy needle comprising:
    a collection chamber having a distal end configured to communicate with a brachytherapy needle;

a first cartridge comprising a plurality of seeds, the first cartridge disposed in communication with the collection chamber; and a second cartridge comprising a plurality of spacers, the second cartridge disposed in communication with the collection chamber, wherein the first and second cartridges further comprise indicia corresponding to quantity of seeds or spacers contained therein.

24. Apparatus for loading therapeutic materials into a brachytherapy needle comprising:

a collection chamber having a distal end configured to communicate with a brachytherapy needle;

a first cartridge comprising a plurality of seeds, the first cartridge disposed in communication with the collection chamber;

a second cartridge comprising a plurality of spacers, the second cartridge disposed in communication with the collection chamber; and means for wrapping the seeds and spacers of the collection chamber in a bio-compatible member.

25. The apparatus of claim 24 wherein the bio-compatible member is bio-absorbable.

26. The apparatus of claim 24 wherein the bio-compatible member comprises means for retaining seeds or spacers wrapped therein.

27. Apparatus for loading therapeutic materials into a brachytherapy needle comprising:

a collection chamber having a distal end configured to communicate with a brachytherapy needle;

a first cartridge comprising a plurality of seeds, the first cartridge disposed in communication with the collection chamber; and a second cartridge comprising a plurality of spacers, the second cartridge disposed in communication with the collection chamber, wherein the collection chamber further comprises means for viewing, removing, or manipulating the contents of the collection chamber.

28. Apparatus for loading therapeutic materials into a brachytherapy needle comprising:

a collection chamber having a distal end configured to communicate with a brachytherapy needle;

a first cartridge comprising a plurality of seeds, the first cartridge disposed in communication with the collection chamber; and a second cartridge comprising a plurality of spacers, the second cartridge disposed in communication with the collection chamber, wherein the collection chamber further comprises means for providing radiation protection from the radioactive seeds contained in the collection chamber.

29. Apparatus for loading therapeutic materials into a brachytherapy needle comprising:

a collection chamber having a distal end configured to communicate with a brachytherapy needle;

a first cartridge comprising a plurality of seeds, the first cartridge disposed in communication with the collection chamber; and a second cartridge comprising a plurality of spacers, the second cartridge disposed in communication with the collection chamber, wherein the collection chamber further comprises means for measuring radiation from the radioactive seeds contained therein.

30. A method of preparing therapeutic materials for loading into a brachytherapy needle comprising:

providing apparatus comprising first and second loading chambers, a first cartridge comprising a plurality of radioactive seeds, the first cartridge disposed in communication with the first loading chamber, a second cartridge comprising a plurality of spacers, the second cartridge disposed in communication with the second loading chamber, a collection chamber having a proximal end in communication with the first and second loading chambers and a distal end adapted to communicate with a brachytherapy needle, the collection chamber configured to receive seeds and spacers from the first and second loading chambers, a plunger configured for reciprocation through the collection chamber, and a brachytherapy needle;

providing a reciprocating first loading stylet proximal to the first loading chamber and a reciprocating second loading stylet proximal to the second loading chamber;

coupling the distal end of the collection chamber within a lumen of a brachytherapy needle; and depositing a seed or a spacer into the first and second loading chambers from the first and second cartridges, respectively.

31. The method of claim 30 further comprising:

providing a first loading stylet proximal to the first loading chamber and second loading stylet proximal to the second loading chamber;

distally advancing the first loading stylet to push a radioactive seed in the first loading chamber into the distal end of the collection chamber; and proximally retracting the first loading stylet, allowing another radioactive seed to be deposited in the first loading chamber from the first cartridge.

32. The method of claim 31 further comprising:

distally advancing the second loading stylet to push a spacer in the second loading chamber into the distal end of the collection chamber; and proximally retracting the second loading stylet, allowing another spacer to be deposited in the second loading chamber from the second cartridge.

33. The method of claim 32 further comprising loading the collection chamber with seeds and spacers in a predetermined packing arrangement.

34. The method of claim 33 further comprising distally advancing the plunger to push the seeds and spacers within the collection chamber into the brachytherapy needle.

* * * * *